US006495154B1

(12) United States Patent
Tam et al.

(10) Patent No.: US 6,495,154 B1
(45) Date of Patent: Dec. 17, 2002

(54) ON DEMAND ADMINISTRATION OF CLOMIPRAMINE AND SALTS THEREOF TO TREAT PREMATURE EJACULATION

(75) Inventors: Peter Tam, Redwood City, CA (US); Neil Gesundheit, Los Altos, CA (US); Leland F. Wilson, Menlo Park, CA (US)

(73) Assignee: Vivus Inc., Mountain View, CA (US)

( * ) Notice: Subject to any disclaimer, the term of this patent is extended or adjusted under 35 U.S.C. 154(b) by 35 days.

(21) Appl. No.: 09/721,412

(22) Filed: Nov. 21, 2000

(51) Int. Cl.[7] .......................... A61F 2/02; A61F 13/02; A61K 9/14; A61K 9/70; A61L 9/04

(52) U.S. Cl. .......................... 424/423; 424/45; 424/46; 424/434; 424/435; 424/443; 424/449; 424/451; 424/464

(58) Field of Search ................................ 424/423, 434, 424/435, 443, 449, 451, 464, 45, 46

(56) References Cited

U.S. PATENT DOCUMENTS

| | | | |
|---|---|---|---|
| 3,467,650 | A | 9/1969 | Schindler et al. |
| 4,507,323 | A | 3/1985 | Stern |
| 4,940,731 | A | 7/1990 | Bick |
| 5,151,448 | A | 9/1992 | Crenshaw et al. |
| 5,276,042 | A | 1/1994 | Crenshaw et al. |
| 5,707,999 | A | 1/1998 | Cavallini |
| 5,830,500 | A | 11/1998 | El-Rashidy et al. |
| 5,922,341 | A | 7/1999 | Smith et al. |

OTHER PUBLICATIONS

Althof et al. (1995), "Double–Blind Crossover Trial of Clomipramine for Rapid Ejaculation in 15 Couples," *J. Clin. Psychiatry* 56(9):402–407.

Althof et al. (1995), "Early Experience with Clomipramine for Rapid Ejaculation," *Proceedings of the American Urological Association* 153:474A.

Assalian (1988), "Clomipramine in the Treatment of Premature Ejaculation," *The Journal of Sex Research* 24:213–215.

Balon (1996), "Antidepressants in the Treatment of Premature Ejaculation," *Journal of Sex and Marital Therapy* 22(2):85–96.

Girgis et al. (1982), "A Double–Blind Trial of Clomipramine in Premature Ejaculation," *Andrologia* 14(4):364–368.

Goodman (1977), "The Management of Premature Ejaculation," *J. Int. Med. Res.* 5(Supplement 1):78–79.

Haensel et al. (1996), "Clomipramine and Sexual Function in Men with Premature Ejaculation and Controls," *The Journal of Urology* 156:1310–1315.

Kim et al. (1998), "Treatment of Premature Ejaculation," *The Journal of Family Practice* 46(4):280–281.

Kim et al. (1998), "Efficacy and Safety of Fluoxetine, Sertraline and Clomipramine in Patients with Premature Ejaculation: A Double–Blind, Placebo Controlled Study," *The Journal of Urology* 159:425–427.

Kolomaznik et al. (1999), "Předčasná Ejakulace" ("Premature Ejaculation"), *C.S. Psychiat.* 95(8):516–523 (English translation included).

Rowland et al. (1998), "The Treatment of Premature Ejaculation: Psychological and Biological Strategies," *Drugs of Today* 34(10):879–899.

Segraves et al. (1993), "Clomipramine versus Placebo in the Treatment of Premature Ejaculation: A Pilot Study," *Journal of Sex & Marital Therapy* 19(3):198–200.

Strassberg et al. (1999), "Clomipramine in the Treatment of Rapid (Premature) Ejaculation," *Journal of Sex & Marital Therapy* 25(2):89–101.

Published: Feb. 2001, Abdel–Hamid et al. (2001), "Assessment of as Needed Use of Pharmacotherapy and the Pause–Squeeze Technique in Premature Ejaculation," *International Journal of Impotence Research* 13(1):41–45.

*Primary Examiner*—Carlos Azpuru
(74) *Attorney, Agent, or Firm*—Reed & Associates; Dianne E. Reed

(57) ABSTRACT

A method is provided for delaying the onset of ejaculation in an individual. The method involves systemic and on demand administration to an individual of a pharmaceutical formulation containing an amount of an active agent selected from the group consisting of clomipramine and pharmacologically acceptable acid addition salts thereof. Drug delivery may be accomplished via any route designed to provide systemic levels of the active agent effective to delay the onset of ejaculation. Pharmaceutical formulations and dosage forms are provided as well.

71 Claims, No Drawings

ON DEMAND ADMINISTRATION OF CLOMIPRAMINE AND SALTS THEREOF TO TREAT PREMATURE EJACULATION

TECHNICAL FIELD

This invention relates generally to methods and pharmaceutical compositions for treating sexual dysfunction; more particularly, the invention relates to treatment of premature ejaculation, preferably by on demand administration of clomipramine or a pharmacologically acceptable acid addition salt thereof.

BACKGROUND

Premature ejaculation is a debilitating sexual dysfunction. This dysfunction can lead to an inability to enter or sustain relationships and can cause psychological damage to sufferers. Premature ejaculation can also impair reproductive success.

Previous methods of treating premature ejaculation included psychological therapies, topical anesthetics and the use of devices (U.S. Pat. Nos. 5,535,758, 5,063,915, 5,327,910, and 5,468,212). All of these methods have significant drawbacks. Psychological therapies benefit only a subset of patients and require specialized therapists who may not be available to all patients, particularly in remote areas. Furthermore, psychological therapies cannot alleviate premature ejaculation resulting from non-psychological causes. Anesthetic agents decrease sensitivity of tissues, thereby diminishing sexual pleasure. Also, topical anesthetics can be transferred to sexual partners and thereby decrease their sensitivity and pleasure as well. With regard to devices, these can be awkward, inconvenient and embarrassing to use. Devices are highly conspicuous, and reveal the very condition which the suffering partner may prefer to conceal. Additionally, devices can cause irritation to one or both partners.

Methods for treating premature ejaculation by systemic administration of several different pharmacologically active compounds have been described (U.S. Pat. Nos. 4,507,323, 4,940,731, 5,151,448, 5,276,042 and 5,707,999; PCT Publication No. WO 95/13072). However, these drugs may not be effective for all patients, and the side effects of these drugs can halt treatment or impair patient compliance. Disease states or adverse interactions with other drugs may contraindicate the use of these compounds or require lower dosages that may not be effective to delay the onset of ejaculation. In addition, many drugs must be administered chronically or at times that are inconvenient.

Oral administration of the antidepressant fluoxetine has been claimed to treat premature ejaculation. However, the administration of fluoxetine has many undesired aspects. U.S. Pat. No. 5,151,448 describes administration of fluoxetine on a daily basis which, according to many clinicians, presents a compliance issue as patients often miss or forget to take their dose. In addition, patients with hepatic or renal impairments may not be able to use fluoxetine due to its metabolism in the liver and excretion via the kidney. Systemic events during oral fluoxetine treatment involving the lungs, kidneys or liver have occurred, and death has occurred from overdoses. In addition, side effects of oral fluoxetine administration include hair loss, nausea, vomiting, dyspepsia, diarrhea, anorexia, anxiety, nervousness, insomnia, drowsiness, fatigue, headache, tremor, dizziness, convulsions, sweating, pruritis and skin rashes. Fluoxetine interacts with a range of drugs, often by impairing their metabolism by the liver.

U.S. Pat. No. 4,940,731 describes the oral or parenteral administration of sertraline on a daily basis for treating premature ejaculation. It has been recognized that sertraline shares many of the same problems as fluoxetine; see Martindale, *The Extra Pharmacopoeia,* 31st edition, at p. 333 (London: The Royal Pharmaceutical Society, 1996). Sertraline is metabolized in the liver, and is excreted in the urine and feces. Thus, patients with cirrhosis must take lower doses, and caution must be exercised when administering sertraline to patients with renal impairment. Individuals taking monoamine oxidase inhibitors cannot take sertraline due to the risk of toxicity, leading to memory changes, confusion, irritability, chills, pyrexia and muscle rigidity. Side effects resulting from oral sertraline administration include nausea, diarrhea, dyspepsia, insomnia, somnolence, sweating, dry mouth, tremor and mania. Rare instances of coma, convulsions, fecal incontinence and gynecomastia have occurred in patients undergoing sertraline therapy.

U.S. Pat. No. 5,276,042 describes daily administration of paroxetine for the treatment of premature ejaculation. Paroxetine is predominantly excreted in the urine, and decreased doses are recommended in patients with hepatic and renal impairments. Like sertraline, paroxetine cannot be given to patients undergoing treatment with a monoamine oxidase inhibitor. Side effects from oral administration of paroxetine include hyponatremia, asthenia, sweating, nausea, decreased appetite, oropharynx disorder, somnolence, dizziness, insomnia, tremor, anxiety, impaired micturition, weakness and paresthesia.

Administration of the $\alpha_1$-adrenergic blockers has been described to treat psychogenic premature ejaculation. U.S. Pat. No. 5,707,999 describes daily administration of alfuzosine or terazosine. A common side effect of these drugs is postural hypotension. In addition, daily administration increases the possibility of patients suffering from a drug×s undesirable side effects as a result of continuous exposure to the agent.

Oral administration of clomipramine to treat men suffering from premature ejaculation has been described in Strassberg et al. (1999) *J. Sex Marital Ther.* 25(2):89–101. The reference describes "as needed" oral administration "as little as four hours prior to sexual activity." Such a dosing regimen, however, still fails to provide for a flexible and convenient method for treating premature ejaculation.

Thus there is a need for methods and dosage forms for treating premature ejaculation that requires no specialized psychological therapy, can be used conveniently and without embarrassment, and avoids the disadvantages associated with prior therapeutic methods and dosage forms.

SUMMARY OF THE INVENTION

Accordingly, it is a primary object of the invention to address the above-described need in the art by providing a novel method for delaying the onset of ejaculation by systemically administering on demand a pharmaceutical formulation containing an amount of an active agent selected from the group consisting of clomipramine and pharmacologically acceptable acid addition salts thereof effective to delay the onset of ejaculation by the individual during sexual activity.

It is another object of the invention to provide such a method wherein the pharmaceutical formulation is administered less than four hours prior to engaging in sexual activity.

It is a further object of the invention to provide such a method wherein the individual suffers from premature ejaculation.

It is yet a further object of the invention to provide such a method wherein the pharmaceutical formulation is administered orally.

It is another object of the invention to provide such a method wherein the pharmaceutical formulation is administered buccally.

It is a further object of the invention to provide such a method wherein the pharmaceutical formulation is administered transmucosally.

It is still a further object of the invention to provide such a method wherein the pharmaceutical formulation is administered nasally.

It is another object of the invention to provide a dosage form for delaying the onset of ejaculation in a male individual, comprising a rapid-release formulation for systemic absorption containing an amount of an active agent selected from the group consisting of clomipramine and pharmacologically acceptable acid addition salts thereof effective to delay the onset of ejaculation by the individual during sexual activity.

Additional objects, advantages and novel features of the invention will be set forth in part in the description which follows, and in part will become apparent to those skilled in the art upon examination of the following, or may be learned by practice of the invention.

In a first aspect of the invention, a method is provided for delaying the onset of ejaculation, the method comprising systemically administering to the individual on demand a pharmaceutical formulation containing an active agent selected from the group consisting of clomipramine and pharmacologically acceptable acid addition salts thereof. Drug delivery may be accomplished through any route that will provide appreciable systemic levels of clomipramine effective to delay the onset of ejaculation. Thus, drug delivery may be effected by, but not limited to, oral, parenteral, buccal or pulmonary administration.

In a further aspect of the invention, a pharmaceutical dosage form is provided for delaying the onset of ejaculation in a male individual. The dosage form comprises a rapid-release formulation for the systemic absorption of an active agent selected from the group consisting of clomipramine and its pharmacologically acceptable salts. Once absorbed in the individual's circulatory system, the active agent exerts its pharmacologic activity. The amount of active agent administered is an amount effective to delay the onset of ejaculation by the individual during sexual activity. In addition to an effective amount of the active agent, the formulation also comprises a pharmacologically acceptable carrier or vehicle. Optionally, additional components may be incorporated into the formulation as well, e.g., excipients, surfactants, preservatives (e.g., antioxidants), stabilizers, chelating agents, taste-masking agents, and the like, as will be appreciated by those skilled in the art of pharmaceutical formulation preparation and drug delivery. The pharmaceutical dosage form may be any dosage form suitable for systemic absorption and may be, but is not limited to, rapidly disintegrating tablets, effervescent tablets, sublingual tablets, buccal dosage forms, sublingual sprays, gum formulations or inhalers.

DETAILED DESCRIPTION OF THE INVENTION

Overview and Definitions

Before describing the present invention in detail, it is to be understood that this invention is not limited to specific dosage forms, carriers, or the like, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, reference to "an additional active agent" includes a single additional active agent or mixtures of two or more additional active agents, and the like.

In describing and claiming the present invention, the following terminology will be used in accordance with the definitions set out below.

The terms "active agent," "drug" and "pharmacologically active agent" are used interchangeably herein to refer to a chemical material or compound which, when administered to an organism (human or animal) induces a desired pharmacologic effect. Included are derivatives and analogs of those compounds or classes of compounds specifically mentioned which also induce the desired pharmacologic effect. In the context of the present invention, the terms generally refer to clomipramine and its pharmacologically acceptable acid addition salts unless the context clearly indicates otherwise.

By "pharmacologically acceptable" is meant a material that is not biologically or otherwise undesirable, i.e., the material may be administered to an individual along with the selected active agent without causing any undesirable biological effects or interacting in a deleterious manner with any of the other components of the pharmaceutical composition in which it is contained. Similarly, a "pharmacologically acceptable" salt of a compound as provided herein is a salt that is not biologically or otherwise undesirable.

By the term "systemically administered" applicants intend all non-local modes of administration that result in appreciable drug levels in an individual's circulatory system. Thus, a "systemically administered" drug must achieve sufficient levels in an individual's circulatory system before the drug is available to exert its intended pharmacological and therapeutic activity.

"On demand" as in "on demand" administration is meant herein to refer to administration of an active agent immediately prior to sexual activity. Thus, "on demand" administration requires administration of the active agent less than four hours prior to sexual activity. As will be appreciated by those skilled in the art, "on demand" administration must take into account the time necessary for the drug to be absorbed into the individual's circulatory system.

"Rapid release" and "immediate release" dosage forms immediately release drug upon contact with aqueous fluid or tissue.

"Sexual activity" as used herein refers to all sexual activity that may result in ejaculation by a individual. Thus, "sexual activity" includes, but is not limited to, coitus.

"Carriers" or "vehicles" as used herein refer to carrier materials suitable for drug administration. Carriers and vehicles useful herein include any such materials known in the art, e.g., any liquid, gel, solvent, liquid diluent, solubilizer, or the like, which is nontoxic and which does not interact with other components of the composition in a deleterious manner.

By an "effective" amount of a drug or pharmacologically active agent is meant a nontoxic but sufficient amount of the drug or agent to provide the desired effect. As will be pointed out below, the exact amount required will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using only routine experimentation.

"Rapidly disintegrating" as in a "rapidly disintegrating tablet" as used herein refers to a tablet that dissolves or disperses in manner that allows for the absorption of the active agent such that "on demand" administration of the active agent is possible. Thus, many rapidly disintegrating tablets often, but not necessarily, include a disintegrant in the tablet formulation or are otherwise specially designed to quickly disintegrate upon administration.

The Active Agent

The invention, as noted above, involves the administration of clomipramine or a pharmacologically acceptable acid addition salt thereof to an individual in order to delay the onset of ejaculation.

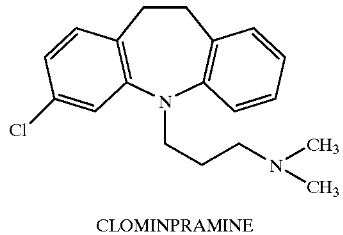

CLOMINPRAMINE

3-Chloro-10,11-dihydro-N,N-dimethyl-5H-dibenz[b,f]azepine-5-propanamine

The active agent may be administered in any form that will delay the onset of ejaculation when administered to an individual. For example, the active agent may be administered as chemically synthesized in the laboratory (e.g., using the methods described in U.S. Pat. No. 3,467,650), or as obtained commercially, e.g., from the Sigma® Chemical Company (St. Louis, Mo., product number C 7291).

The clomipramine and any additional active agents present may be administered in the form of a pharmacologically acceptable salt, analog or combination thereof. Salts of the active agent may be prepared using standard procedures known to those skilled in the art of synthetic organic chemistry and described, for example, by J. March, *Advanced Organic Chemistry: Reactions Mechanisms and Structure,* 4th Ed. (New York: Wiley-Interscience, 1992). For example, acid addition salts are prepared from the free base (typically wherein the neutral form of the drug has a neutral amino group) using conventional means, involving reaction with a suitable acid. Generally, the base form of the drug is dissolved in a polar organic solvent such as methanol or ethanol and the acid is added thereto. The resulting salt either precipitates or may be brought out of solution by addition of a less polar solvent. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Preparation of basic salts of acid moieties which may be present (e.g., carboxylic acid groups) are prepared in a similar manner using a pharmaceutically acceptable base such as sodium hydroxide, potassium hydroxide, ammonium hydroxide, calcium hydroxide, magnesium hydroxide, trimethylamine, or the like.

Analogs and other derivatives of the active agent may be prepared using standard techniques known to those skilled in the art of synthetic organic chemistry, or may be deduced by reference to the pertinent literature.

Preferably, the methods and dosage forms described herein use an acid addition salt form of clomipramine. Furthermore, clomipramine hydrochloride is a particularly preferred acid addition salt.

Rapid-Release Formulations

The rapid-release formulations may be in any form suitable to provide rapid and systemic absorption of the active agent. Although the time necessary for systemic absorption will depend on the particular dosage form used, it is preferred that the formulation and dosage form provide systemically effective levels of and the desired biological response to the active agent less than 4.0, preferably less than 3.5, more preferably less than 3.0, still more preferably less than 2.5, yet more preferably less than 2.0, and yet still more preferably less than 1.5 hours following administration. It is particularly preferred that the formulation and dosage form provide systemically effective levels of the drug and the desired biological response less than 1.0 hour following administration with less than 0.5 hours being most preferred.

Depending on the intended mode of administration, the rapid-release formulations may be in the form of solid, semi-solid, liquid or aerosol dosage forms such as, for example, tablets, including buccal tablets and rapidly disintegrating tablets such as effervescent tablets, sublingual tablets and "open matrix network" tablets, capsules, powders, gums, liquids, suspensions, or the like, preferably in unit dosage form suitable for single administration of a precise dosage. The compositions will include an effective amount of the active agent in combination with a pharmaceutically acceptable carrier and, in addition, may include other pharmaceutical agents, adjuvants, diluents, buffers, etc. The amount of active agent administered will, of course, be dependent on the subject being treated, the subject's weight, the manner of administration and the judgment of the prescribing physician.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington*, cited supra.

For oral administration, the composition will generally take the form of a tablet or capsule, or may be an aqueous or nonaqueous solution, suspension or syrup. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

One type of tablet that provides rapid release is a buccal tablet. Preferred buccal tablets will typically comprise a therapeutically effective amount of the active agent and a bioerodible (hydrolyzable) polymeric carrier that may also serve to adhere the dosage form to the buccal mucosa. The buccal dosage unit is fabricated so as to release at least a portion of the active agent immediately. In addition, the buccal dosage unit may be designed so as to erode gradually over a predetermined time period, wherein drug delivery is provided essentially throughout. Buccal drug delivery, as will be appreciated by those skilled in the art, avoids some of the disadvantages encountered with oral modes of administration, e.g., slow absorption, degradation of the active agent by fluids present in the gastrointestinal tract and/or first-pass inactivation in the liver. The "effective amount" of clomipramine or salt thereof in the dosage unit will of course depend, inter alia, on the intended dosage, which, in turn, is dependent on the particular individual undergoing treatment, the specific indication, and the like. The dosage unit will generally contain from approximately 1.0 wt. % to about 60 wt. % active agent, preferably on the order of 1 wt. % to about 30 wt. % active agent. With regard to the bioerodible (hydrolyzable) polymeric carrier, it will be appreciated that virtually any such carrier can be used, so long as the desired drug release profile is not compromised, and the carrier is compatible with the active agent to be administered and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and copolymers, e.g., those known as "carbomers" (Carbopol®, which may be obtained from B.F. Goodrich, is one such polymer). Other suitable polymers include, but are not limited to: hydrolyzed polyvinylalcohol; polyethylene oxides (e.g., Sentry Polyox® water soluble resins, available from Union Carbide); polyacrylates (e.g., Gantrez®, which may be obtained from GAF); vinyl polymers and copolymers; polyvinylpyrrolidone; dextran; guar gum; pectins; starches; and cellulosic polymers such as hydroxypropyl methylcellulose, (e.g., Methocel®, which may be obtained from the Dow Chemical Company), hydroxypropyl cellulose (e.g., Klucel®, which may also be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methyl cellulose, ethyl cellulose, cellulose acetate phthalate, cellulose acetate butyrate, and the like.

Other components may also be incorporated into the buccal dosage forms described herein. The additional components include, but are not limited to, disintegrants, diluents, binders, lubricants, flavorings, colorants, preservatives, and the like. Examples of disintegrants that may be used include, but are not limited to, cross-linked polyvinylpyrrolidones, such as crospovidone (e.g., Polyplasdone® XL, which may be obtained from GAF), cross-linked carboxylic methylcelluloses, such as croscarmelose (e.g., Ac-di-sol®, which may be obtained from FMC), alginic acid, and sodium carboxymethyl starches (e.g., Explotab®, which may be obtained from Edward Medell Co., Inc.), methylcellulose, agar bentonite and alginic acid. Suitable diluents are those that are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pak®, which may be obtained from Amstar), lactose, calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Particularly preferred lubricants are stearates and stearic acid, and an optimal lubricant is magnesium stearate.

Preferred sublingual dosage forms include sublingual tablets, creams, ointments and pastes with sublingual tablets being particularly preferred. The tablet, cream, ointment or paste for sublingual delivery comprises a therapeutically effective amount of the selected active agent and one or more conventional nontoxic carriers suitable for sublingual drug administration. The sublingual dosage forms of the present invention can be manufactured using conventional processes. The sublingual dosage unit is fabricated to disintegrate rapidly. The time period for complete disintegration of the dosage unit is typically in the range of from about 10 seconds to about 30 minutes, and optimally is less than 5 minutes.

With regard to sublingual tablets, these tablets are generally small in size and intended to be dissolved under the tongue for absorption through the oral mucosa for systemic circulation. Sublingual tablets generally comprise a formulation containing drug and a pharmaceutically acceptable sugar, e.g., lactose, galactose, sucrose, mannose, glucose, ribose, xylose and combinations thereof, as a carrier. The formulation is then compressed into tablets using conventional techniques well-known in the art.

Other components may also be incorporated into the sublingual dosage forms described herein. The additional components include, but are not limited to binders, disintegrators, wetting agents, lubricants, and the like. Examples of binders that may be used include water, ethanol, polyvinylpyrrolidone, starch solution gelatin solution, and the like. Suitable disintegrators include dry starch, calcium carbonate, polyoxyethylene sorbitan fatty acid esters, sodium lauryl sulfate, stearic monoglyceride, lactose, and the like. Wetting agents, if used, include glycerin, starches, and the like. Particularly preferred lubricants are stearates and polyethylene glycol. Additional components that may be incorporated into sublingual dosage forms are known, or will be apparent, to those skilled in this art; for example, see *Remington*, cited supra.

In addition to sublingual tablets, other rapidly disintegrating tablets are preferred. Examples of such tablets are well-known in the art. Another preferred rapidly disintegrating tablet includes effervescent tablets. Effervescent tablets are described in *Remington*, supra, and examples may be found in the literature, and in, for example, U.S. Pat. No. 5,211,957 to Hagemann et al. Generally, effervescent tablets contain the active agent in combination with additives such as sodium bicarbonate and an organic acid. e.g., tartaric acid or citric acid. In the presence of water, these additives react to liberate carbon dioxide thereby facilitating the disintegration of the tablet. Once the tablet is substantially disintegrated, an individual swallows the resultant solution thereby providing systemic adsorption of the active agent.

Another version of a rapidly disintegrating tablet includes "open matrix network" tablets. These tablets can disintegrate within seconds, i.e., within five to ten seconds, after being placed on the tongue of an individual. The contents of the tablet can then be swallowed with or without water. An example of such a tablet is found in U.S. Pat. No. 4,371,516 to Gregory et al. As described therein, the carrier provides a low density network, e.g., about 10 to about 200 mg/cm$^3$, of water-soluble or water-dispersible material. The tablet is produced by subliming a solution containing both the drug and carrier that is subsequently directed to a mold having tablet-shaped depressions. The carrier may be any suitable material, but is preferably gelatin, with partially hydrolyzed gelatin most preferred. Other examples of rapidly disintegrating tablets that can be adapted to contain clomipramine are well-known in the art. See, for example, U.S. Pat. No. 5,776,492 to Betzing et al.

The active agent may be administered via a sublingual spray or inhaled. Sublingual sprays and inhalers are prepared according to techniques well-known in the art of pharmaceutical formulation and may be prepared as solutions in saline, employing benzyl alcohol or other suitable preservatives, absorption promoters to enhance bioavailability, propellants such as fluorocarbons or nitrogen, and/or other conventional solubilizing or dispersing agents.

In addition, the active agent may be administered via a chewing gum formulation. Gum formulations containing a pharmacologically active agent and techniques for preparing such formulations are well-known in the art. For example, a gum base (available commercially from, for example, Cafosa, Inc., Calabria, Spain) is rolled in a suitable roller at about 10 to 85° C. for about three minutes. Thereafter, all components except for the active agent, e.g., plasticizers, sugars, sweeteners, fillers, polymers and waxes, are added sequentially and rolled until a homogenous material is obtained. Then, active agent is added and rolled until the entire material is homogenous. Once homogenous, the material is removed from the roll, cooled to room temperature and processed into the desired gum shape, e.g., cubes or sticks.

The active agent may also be administered intranasally, for example in a solution, using drops or a spray. Nasal solutions are generally prepared so that they are isotonic and slightly buffered to have a pH of about 5.5 to 6.5. The solutions includes a suitable liquid carrier, e.g., a saline solution, and may also include antimicrobial preservatives, drug stabilizers, and other additives known to those of ordinary skill in the art of pharmaceutical formulation. Intranasal administration may also involve use of a dry powder spray, although administration of a solution is preferred.

The pharmaceutical formulation may include an additional active agent. Examples of additional active agents include, but are not limited to:

antidepressants including amesergide, amineptine, amitriptyline, amoxapine, benactyzine, brofaromine, bupropion, butriptyline, cianopramine, citalopram, clorgyline, clovoxamine, demexiptiline, desipramine, dibenzepin, dimetacrine, dothiepin, doxepin, etoperidone, femoxetine, fezolamine, fluoxetine, fluvoxamine, ifoxetine, imipramine, iprindole, isocarboxazid, levoprotiline, lofepramine, maprotiline, medifoxamine, melitracen, metapramine, methylphenidate, mianserin, milnacipran, minaprine, mirtazapine, moclobemide, nefazodone, nialamide, nomifensine, nortriptyline, opipramol, oxaflozane, oxaprotiline, oxitriptan, paroxetine, phenelzine, pirlindole, propizepine, protriptyline, quinupramine, rolipram, selegiline, sertraline, setiptiline, sibutramine, teniloxazine, tianeptine, tofenacin, toloxatone, tranylcypromine, trazodone, trimipramine, tryptophan, venlafaxine, viloxazine, viqualine and zimeldine;

serotonin agonists including 2-methyl serotonin, buspirone, ipsaperone, tiaspirone, gepirone, lysergic acid diethylamide, ergot alkaloids, 8-hydroxy-(2-N,N-dipropylamino)-tetraline, 1-(4-bromo-2,5-dimethoxyphenyl)-2-aminopropane, cisapride, sumatriptan, m-chlorophenylpiperazine, trazodone, zacopride and mezacopride;

serotonin antagonists including ondansetron, granisetron, metoclopramide, tropisetron, dolasetron, trimethobenzamide, methysergide, risperidone, ketanserin, ritanserin, clozapine, amitryptiline, R(+)-α-(2,3-dimethoxyphenyl)-1-[2-(4-fluorophenyl)ethyl]-4-piperidine-methanol, azatadine, cyproheptadine, fenclonine, dexfenfluramine, fenfluramine, chlorpromazine and mianserin;

adrenergic agonists including methoxamine, methpentermine, metaraminol, mitodrine, clonidine, apraclonidine, guanfacine, guanabenz, methyldopa, amphetamine, methamphetamine, epi-nephrine, norepinephrine, ethylnorepinephrine, phenylephrine, ephedrine, pseudo-ephedrine, methylphenidate, pemoline, naphazoline, tetrahydrozoline, oxymetazoline, xylometazoline, phenylpropanolamine, phenylethylamine, dopamine, dobutamine, colterol, isoproterenol, isotharine, metaproterenol, terbutaline, metaraminol, tyramine, hydroxy-amphetamine, ritodrine, prenalterol, albuterol, isoetharine, pirbuterol, bitolterol, fenoterol, formoterol, procaterol, salmeterol, mephenterine and propylhexedrine;

adrenergic antagonists including phenoxybenzamine, phentolamine, tolazoline, prazosin, terazosin, doxazosin, trimazosin, yohimbine, ergot alkaloids, labetalol, ketanserin, urapidil, alfuzosin, bunazosin, tamsulosin, chlorpromazine, haloperidol, phenothiazines, butyrophenones, pro-pranolol, nadolol, timolol, pindolol, metoprolol, atenolol, esmolol, acebutolol, bopindolol, carteolol, oxprenolol, penbutolol, carvedilol, medroxalol, naftopidil, bucindolol, levobunolol, metipranolol, bisoprolol, nebivolol, betaxolol, carteolol, celiprolol, sotalol, propafenone and indoramin;

adrenergic neurone blockers including bethanidine, debrisoquine, guabenxan, guanadrel, guanazodine, guanethidine, guanoclor and guanoxan;

benzodiazepines including alprazolam, brotizolam, chlordiazepoxide, clobazepam, clonazepam, clorazepate, demoxepam, diazepam, estazolam, flurazepam, halazepam, lorazepam, midazolam, nitrazepam, nordazapam, oxazepam, prazepam, quazepam, temazepam and triazolam.

Particularly preferred additional active agents include benzodiazepines such as those listed above and selective serotonin reuptake inhibitors (SSRIs), e.g., fluoxetine, fluvoxamine, paroxetine and sertraline.

Some agents, as may be seen, are encompassed by more than one of the above categories, e.g., serotonin antagonists and antidepressants, or serotonin agonists and antagonists.

In addition to the active agent, the formulation, particularly when present in a gum or oral, buccal or sublingual tablet, will generally contain other materials such as binders, diluents, lubricants, disintegrants, fillers, stabilizers, surfactants, coloring agents, taste-masking agents, and the like. Binders are used to impart cohesive qualities to the formulation; suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, hydroxyethyl cellulose, and the like), and Veegum®. As will be appreciated by those skilled in the art, binders, if present, must not delay disintegration of the formulation to such an extent that "on demand" administration is ineffective. Diluents are typically necessary to increase bulk so that a dosage form of practical size is ultimately provided. Suitable diluents include dicalcium phosphate, calcium sulfate, lactose, cellulose, kaolin, mannitol, sodium chloride, dry starch and powdered sugar. Lubricants are used to facilitate manufacture of the dosage form; examples of suitable lubricants include, for example, magnesium stearate, calcium stearate, and stearic acid. Stearates, if present, preferably represent at no more than approximately 2 wt. % of the formulation. Disintegrants are used to facilitate disintegration of the dosage form, and are generally starches, clays, celluloses, algins, gums or crosslinked polymers; sodium starch glycolate is particularly preferred. Fillers include, for example, insoluble materials such as silicon dioxide, titanium dioxide, alumina, talc, kaolin, powdered cellulose, microcrystalline cellulose, and the like, as well as soluble materials such as mannitol, urea, sucrose, lactose, dextrose, sodium chloride, sorbitol, and the like. Stabilizers are used to inhibit or retard drug decomposition reactions which include, by way of example, oxidative reactions. Surfactants include anionic, cationic, amphoteric and nonionic surface active agents, with anionic surfactants preferred. Suitable anionic surfactants include, but are not limited to, those containing carboxylate, sulfonate and sulfate ions, associated with cations such as sodium, potassium, and ammonium ions. Particularly preferred surfactants include long alkyl chain sulfonates and alkyl aryl sulfonates such as sodium dodecylbenzene sulfonate; dialkyl sodium sulfosuccinates, such as sodium bis-(2-ethylhexyl) sulfosuccinate; and alkyl sulfates such as sodium lauryl sulfate. Taste-masking agents, i.e., flavorants, are used to disguise a bitter or undesirable taste of a component and/or impart a pleasant flavor to a pharmaceutical preparation. Particularly preferred taste-masking agents include sugars (e.g., glucose, sucrose, fructose and sorbitol), anise oil, cinnamon oil, cocoa, menthol, orange oil, peppermint oil and vanillin.

Utility and Modes of Administration

The invention provides for formulations and methods that are effective in delaying the onset of ejaculation. The present formulations are administered on demand, i.e., less than four hours prior to engaging in sexual activity. On demand administration also includes administration at almost any time within the four hour window immediately prior to engaging in sexual activity. Thus, for some dosage forms, e.g., the sublingual spray, on demand administration may take place even 10 minutes prior to engaging in sexual activity. Such flexibility in administration is desirable since the individual may administer the formulation at any convenient time within the four hour window leading up to sexual activity. In addition, because they are all systemically acting, the formulations may be discreetly administered without need for a device, thereby avoiding potential embarrassment.

Typically, although not necessarily, the individual seeking to delay the onset of ejaculation suffers from premature ejaculation. In accordance with the invention, administration of clomipramine results in systemic levels of the drug sufficient to delay the onset of ejaculation. It is preferred that the pharmaceutical formulation is administered orally, buccally or transmucosally. As will be appreciated by those skilled in the art, tablets, including effervescent tablets and "open matrix network" tablets, are administered orally. These formulations are absorbed in the gastrointestinal tract, although some absorption will take place in the oral mucosa. Buccal tablets are placed in the "cheek pouch" wherein absorption of clomipramine primarily takes place transmucosally, primarily in the buccal mucosa. Sublingual sprays and sublingual tablets are administered under the tongue providing for rapid absorption of clomipramine transmucosally, primarily in the vascularized region under the tongue. Inhaled formulations are administered orally (tracheally) for absorption through pulmonary tissues. Gum formulations containing the active agent are chewed, thereby releasing the active agent. Once released from the gum formulation, the active agent forms a solution in the oral cavity for absorption through the oral mucosa and gastrointestinal tract when the solution is swallowed by the individual. As will be appreciated by those skilled in the art, each of these modes of administration are not "local" in nature and will result in systemic levels of the active agent.

As stated above, the amount of active agent administered, and the dosing regimen used, will, of course, be dependent on, inter alia, the age and general condition of the individual being treated, the degree to which the onset of ejaculation is to be delayed, and the judgment of the prescribing physician. The dose is administered on demand. That is, administration will occur less than 4.0, preferably less than 3.5, more preferably less than 3.0, still more preferably less than 2.5, yet more preferably less than 2.0, yet still more preferably less than 1.5 hours prior to engaging in sexual activity. It is particularly preferred that administration occurs less than 1.0 hour before engaging in sexual activity with less than 0.5 hours being most preferred. As is appreciated by those skilled in the art, the methods and dosage forms of the invention relate to systemic administration. In order to achieve systemically effective levels of the drug, a typical on demand dose of the active agent is generally in the range of from about 1 mg to about 300 mg, preferably of from about 20 mg to about 200 mg with a dose in the range of from about 25 mg to about 100 mg being most preferred. Thus, unit dose forms preferably contain the active agent in these ranges as well, i.e., from about 1 mg to about 300 mg, more preferably from about 20 mg to about 200 mg with about 25 mg to about 100 mg of active agent in each unit dose form. The dosing regimen can be modulated in order to achieve satisfactory control of the onset of ejaculation.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

Experimental

The practice of the present invention will employ, unless otherwise indicated, conventional techniques of pharmaceutical formulation and the like, which are within the skill of the art. Such techniques are fully explained in the literature. In the following examples, efforts have been made to ensure accuracy with respect to numbers used (e.g., amounts, temperatures, etc.) but some experimental error and deviation should be accounted for. Unless otherwise indicated, temperature is in degrees C and pressure is at or near atmospheric pressure at sea level. All reagents were obtained commercially unless otherwise indicated.

EXAMPLE 1

An effervescent tablet is prepared containing the following components:

| Component | Amount (per tablet) |
|---|---|
| Clomipramine hydrochloride | 300 mg |
| Sodium bicarbonate | 1985 mg |
| Citric acid | 1000 mg |

The components (i.e., clomipramine hydrochloride, sodium bicarbonate and citric acid, as set forth in the above table) are thoroughly mixed. An effervescent tablet is produced by placing the mixture in a die followed by compression with an appropriate punch. Relatively little compression force is used, e.g., about 3,000 to about 20,000 pounds of force.

EXAMPLE 2

A buccal tablet is prepared containing the following components:

| Component | Amount (per tablet) |
|---|---|
| Clomipramine hydrochloride | 10 mg |
| Gelatin | 90 mg |
| Glycerin (concentrated) | 20 mg |
| Lactose | 10 mg |
| Mannitol | 20 mg |

Clomipramine hydrochloride (10 g) and 90 g of gelatin are mixed and pulverized in a mill. After the mixing is complete, 20 g of concentrated glycerin, 10 g of lactose and 20 g of mannitol are added and the components are mixed until uniform. 150 mg aliquot portions of the mixture are compression-molded to provide a buccal dosage unit. Each buccal unit contains 10 mg of clomipramine hydrochloride.

EXAMPLE 3

A sublingual tablet is prepared containing the following components:

| Component | Amount (% by weight) |
|---|---|
| Clomipramine hydrochloride | 35% |
| Lactose | 63.67% |
| Polyethylene glycol 3350 | 1.0% |
| Magnesium stearate | 0.33% |

The components (i.e., clomipramine hydrochloride, lactose, polyethylene glycol 3350 and magnesium stearate, as set forth in the above table) are thoroughly mixed. A sublingual tablet is produced by placing the mixture in a die followed by compression with an appropriate punch. Relatively little compression force is used, e.g., about 3,000 to about 20,000 pounds of force.

EXAMPLE 4

An “open matrix network” tablet is prepared. A solution containing the following components is prepared:

| Component | Amount |
|---|---|
| Clomipramine hydrochloride | 50 g |
| Partially hydrolyzed gelatin | q.s. to 1,000 ml |

A metal mold containing cylindrical depressions (each depression is about 0.5 cm in diameter and about 1.0 cm deep) is cooled to about −192° C. with liquid nitrogen. The clomipramine is mixed with the partially hydrolyzed gelatin solution. With continuous mixing, 0.5 ml of the solution is transferred into each depression. After the solution freezes, the mold is placed in a vacuum chamber at room temperature under a vacuum of 0.3 mm Hg for 12 hours. The dosage forms, each containing about 25 mg of the active agent, are then removed from the molds. The dosage forms disintegrate rapidly, i.e., from about five to ten seconds when administered orally.

EXAMPLE 5

A solution for use in a sublingual spray or pulmonary inhaler is prepared. The solution is prepared according to the following:

| Component | Amount |
|---|---|
| Clomipramine hydrochloride | 2.5 g |
| Benzalkonium chloride | 0.100 g |
| Distilled water | q.s. to 100 ml |

The formulation is prepared by initially forming a clomipramine hydrochloride solution by combining, under aseptic conditions, 2.5 g of clomipramine hydrochloride in 50 ml of distilled water. Sodium chloride may be added such that the final solution is isotonic. The amount of sodium chloride necessary to provide a final isotonic solution can be calculated based on equations provided in the literature or can be determined experimentally by those skilled in the art. Benzalkonium chloride is used as a preservative and is added to the solution followed by mixing.

The solution is then placed into a spray bottle which typically comprises a collapsible container vessel, an applicator and a cap. For sublingual sprays, the applicator is shaped and sized to be received under the tongue. For pulmonary administration, the applicator is shaped and sized to facilitate tracheal inhalation by an individual. The applicator will have an opening to release a spray or mist of the solution.

The spray bottle is designed to deliver an individual dose with one to three compressions of the bottle to deliver an effective dose. For example, one compression of the bottle may be designed to administer approximately 0.33 ml of liquid as a mist or spray. In the context of the formulation described above housed in such a bottle, one or more compressions of the bottle will provide an effective dose of clomipramine.

EXAMPLE 6

A gum formulation is prepared. The components of the gum formulation are as follows:

| Component | Amount (% by weight) |
|---|---|
| Clomipramine hydrochioride | 2% to 30% |
| Gum base (Cafosa TAB-3-T, available from Cafosa, Inc., Calabria, Spain) | 15% to 50% |
| Sorbitol powder | 10% to 50% |

Cafosa gum base TAB-3-T is rolled in a suitable roller at about 45° C. for about three minutes. Thereafter, the sorbitol powder is added and rolled for about four minutes to obtain a homogenous mixture. Clomipramine hydrochloride is then added to and rolled with the material for another three minutes. The rolled material is removed from the rolling equipment, cooled to room temperature and processed into the small cubes. Each cube contains a therapeutically effective amount of the active agent.

EXAMPLE 7

The patients for the study are drawn from a waiting list for psychosexual therapy of a sexology outpatient department and through advertisement. The inclusion criteria are that the patients be heterosexual, be aged 18–75 years, be involved in a sexual relationship with a female partner during the previous 6 months, the partner is able to participate in the study, and the patient experiences premature ejaculation.

Patients are excluded if they used psychoactive medication, are receiving any therapy for sexual dysfunction, have inhibited male orgasm, are alcohol or substance abusers, score greater than 14 on the 24-item Hamilton Rating Scale for Depression (HAM-D) indicating clinically significant depression, and for other clinically significant medical disease or symptomatology. For the duration of the study, the patients are required to abstain from alcohol.

Patients are randomly assigned to double-blind treatment with any rapid-release formulation described in the examples or a placebo. Patients who remain in the study for at least 3 weeks are included in the statistical analysis. Patients are provided with formulations prepared in the preceding Examples for administration or matching placebo. Patients are instructed to administer the formulation at any time within the four hour window leading up to anticipated sexual activity. During the study, the patients do not use condoms or topical anesthetics.

Patients and their partners are assessed at the end of each week. Efficacy measures include (1) frequency of attempted intercourse, (2) latency to attempted ejaculation (from penetration), (3) frequency of successful attempts at intercourse without premature ejaculation, (4) number of incidences of premature ejaculation, and (5) time to ejaculation as reported by both the patients and their partners based on subjective measurements. In addition, the patients are assessed using the following psychopathological rating instruments: Hamilton Depression Rating Scale (HDRS), Clinical Global Impression (CGI), COVI Anxiety Scale, Atypical Depressive Disorders Scale-Changes (ADDS-C) and an adverse event form.

The response to treatment is scored. The mean or median values are analyzed by using parametric tests including Friedman two-way analysis of variance (ANOVA) and the Wilcoxon matched-pairs signed-ranks test to assess differences in measurements within the groups, and the Mann-Whitney test for differences between the groups. Differences between groups on discrete variables are tested for statistical significance by using Fisher's exact test. A two-tailed p value$\leqq$0.05 is considered significant for these analysis.

Each of the formulations prepared and administered for systemic absorption is expected to be effective in treating premature ejaculation. The use of the formulations results in an extension of intravaginal ejaculation latency time in patients with premature ejaculation. The data from patient-rated and partner-rated latency to ejaculation is compared. Both of these parameters show greater improvement with clomipramine-containing formulations as compared to placebo. In addition, those patients who attempted to treat their premature ejaculation with previous modalities report greater satisfaction with on demand administration of the formulations provided in the examples. Specifically, these patients cited greater flexibility with the timing of the dose, less side effects (in part due to not administering clomipramine on a daily basis) and less embarrassment.

We claim:

1. A method for delaying the onset of ejaculation in a male individual, comprising systemically administering to the individual, less than 3.5 hours prior to engaging in sexual activity, a rapid-release pharmaceutical formulation containing an active agent selected from the group consisting of clomipramine and pharmacologically acceptable acid addition salts thereof, in an amount effective to delay the onset of ejaculation by the individual during sexual activity, wherein the formulation releases the active agent at a rate that provides a systemically effective level of the agent within 3.5 hours of administration.

2. The method of claim 1, wherein the active agent is clomipramine.

3. The method of claim 1, wherein the active agent is an acid addition salt of clomipramine.

4. The method of claim 3, wherein the active agent is clomipramine hydrochloride.

5. The method of claim 1, wherein the pharmaceutical formulation is administered less than 3.0 hours prior to engaging in sexual activity.

6. The method of claim 5, wherein the pharmaceutical formulation is administered less than 2.5 hours prior to engaging in sexual activity.

7. The method of claim 6, wherein the pharmaceutical formulation is administered less than 2.0 hours prior to engaging in sexual activity.

8. The method of claim 7, wherein the pharmaceutical formulation is administered less than 1.5 hours prior to engaging in sexual activity.

9. The method of claim 8, wherein the pharmaceutical formulation is administered less than 1.0 hour prior to engaging in sexual activity.

10. The method of claim 9, wherein the pharmaceutical formulation is administered less than 0.5 hours prior to engaging in sexual activity.

11. The method of claim 1, wherein the pharmaceutical formulation is administered orally.

12. The method of claim 1, wherein the pharmaceutical formulation is administered buccally.

13. The method of claim 1, wherein the pharmaceutical formulation is administered sublingually.

14. The method of claim 1, wherein the pharmaceutical formulation is administered intranasally.

15. The method of claim 1, wherein the active agent is administered in an amount of from about 1 mg to about 300 mg.

16. The method of claim 15, wherein the active agent is administered in an amount of from about 20 mg to about 200 mg.

17. The method of claim 16, wherein the active agent is administered in an amount of from about 25 mg to about 100 mg.

18. The method of claim 1, wherein the individual suffers from premature ejaculation.

19. The method of claim 1, wherein the formulation further comprises an additional active agent.

20. The method of claim 19, wherein the additional active agent is selected form the group consisting of amesergide, amineptine, amitriptyline, amoxapine, benactyzine, brofaromine, bupropion, butriptyline, cianopramine, citalopram, clorgyline, clovoxamine, demexiptiline, desipramine, dibenzepin, dimetacrine, dothiepin, doxepin, etoperidone, femoxetine, fezolamine, fluoxetine, fluvoxamine, ifoxetine, imipramine, iprindole, isocarboxazid, levoprotiline, lofepramine, maprotiline, medifoxamine, melitracen, metapramine, methylphenidate, mianserin, milnacipran, minaprine, mirtazapine, moclobemide, nefazodone, nialamide, nomifensine, nortriptyline, opipramol, oxaflozane, oxaprotiline, oxitriptan, paroxetine, phenelzine, pirlindole, propizepine, protriptyline, quinupramine, rolipram, selegiline, sertraline, setiptiline, sibutramine, teniloxazine, tianeptine, tofenacin, toloxatone, tranylcypromine, trazodone, trimipramine, tryptophan, venlafaxine, viloxazine, viqualine, zimeldine, 2-methyl serotonin, buspirone, ipsaperone, tiaspirone, gepirone, lysergic acid diethylamide, ergot alkaloids, 8-hydroxy-(2-N,N-dipropylamino)-tetraline, 1-(4-bromo-2, 5-dimethoxyphenyl)-2-aminopropane, cisapride, sumatriptan, m-chlorophenylpiperazine, zacopride, mezacopride, ondansetron, granisetron, metoclopramide, tropisetron, dolasetron, trimethobenzamide, methysergide, risperidone, ketanserin, ritanserin, clozapine, amitryptiline, R(+)-α-(2,3-dimethoxyphenyl)-1-[2-(4-fluorophenyl) ethyl]-4-piperidine-methanol, azatadine, cyproheptadine, fenclonine, dexfenfluramine, fenfluramine, chlorpromazine, methoxamine, methpentermine, metaraminol, mitodrine, clonidine, apraclonidine, guanfacine, guanabenz, methyldopa, amphetamine, methamphetamine, epinephrine, norepinephrine, ethylnorepinephrine, phenylephrine, ephedrine, pseudo-ephedrine, pemoline, naphazoline, tetrahydrozoline, oxymetazoline, xylometazoline, phenylpropanolamine, phenylethylamine, dopamine, dobutamine, colterol, isoproterenol, isotharine, metaproterenol, terbutaline, tyramine, hydroxyamphetamine, ritodrine, prenalterol, albuterol, isoetharine, pirbuterol, bitolterol, fenoterol, formoterol, procaterol, salmeterol, mephenterine, propylhexedrine, phenoxybenzamine, phentolamine, tolazoline, prazosin, terazosin, doxazosin, trimazosin, yohimbine, labetalol, urapidil, alfuzosin, bunazosin, tamsulosin, chlorpromazine, haloperidol, phenothiazines, butyrophenones, pro-pranolol, nadolol, timolol, pindolol, metoprolol, atenolol, esmolol, acebutolol, bopindolol, carteolol, oxprenolol, penbutolol, carvedilol, medroxalol, naftopidil, bucindolol, levobunolol, metipranolol, bisoprolol, nebivolol, betaxolol, carteolol, celiprolol, sotalol, propafenone, indoramin, bethanidine, debrisoquine, guabenxan, guanadrel, guanazodine, guanethidine, guanoclor, guanoxan, alprazolam, brotizolam, chlordiazepoxide, clobazepam, clonazepam, clorazepate, demoxepam, diazepam, estazolam, flurazepam, halazepam, lorazepam, midazolam, nitrazepam, nordazapam, oxazepam, prazepam, quazepam, temazepam, triazolam, pharmaceutically acceptable salts thereof, and combinations of any of the foregoing.

21. The method of claim 20, wherein the additional active agent is selected from the group consisting of alprazolam, brotizolam, chlordiazepoxide, clobazepam, clonazepam, clorazepate, demoxepam, diazepam, estazolam, flurazepam, halazepam, lorazepam, midazolam, nitrazepam, nordazapam, oxazepam, prazepam, quazepam, temazepam, triazolam, and pharmaceutically acceptable salts thereof.

22. The method of claim 20, wherein the additional active agent is selected from the group consisting of fluoxetine, fluvoxamine, paroxetine, sertraline, and pharmaceutically acceptable salts thereof.

23. A method for delaying the onset of ejaculation in a male individual, comprising systemically administering to the individual, on demand, a pharmaceutical formulation containing an active agent selected from the group consisting of pharmacologically acceptable acid addition salts of clomipramine, in an amount effective to delay the onset of ejaculation by the individual during sexual activity.

24. The method of claim 23, wherein the pharmaceutical formulation is administered less than 4.0 hours prior to engaging in sexual activity.

25. The method of claim 24, wherein the pharmaceutical formulation is administered less than 3.5 hours prior to engaging in sexual activity.

26. The method of claim 25, wherein in the pharmaceutical formulation is administered less than 3.0 hours prior to engaging in sexual activity.

27. The method of claim 26, wherein the pharmaceutical formulation is administered less than 2.5 hours prior to engaging in sexual activity.

28. The method of claim 27, wherein the pharmaceutical formulation is administered less than 2.0 hours prior to engaging in sexual activity.

29. The method of claim 28, wherein the pharmaceutical formulation is administered less than 1.5 hours prior to engaging in sexual activity.

30. The method of claim 29, wherein the pharmaceutical formulation is administered less than 1.0 hour prior to engaging in sexual activity.

31. The method of claim 30, wherein the pharmaceutical formulation is administered less than 0.5 hours prior to engaging in sexual activity.

32. The method of claim 23, wherein the pharmaceutical formulation is administered orally.

33. The method of claim 23, wherein the pharmaceutical formulation is administered buccally.

34. The method of claim 23, wherein the pharmaceutical formulation is administered sublingually.

35. The method of claim 23, wherein the pharmaceutical formulation is administered intranasally.

36. The method of claim 23, wherein the active agent is administered in an amount of from about 1 mg to about 300 mg.

37. The method of claim 23, wherein the individual suffers from premature ejaculation.

38. The method of claim 23, wherein the formulation further comprises an additional active agent.

39. A method for delaying the onset of ejaculation in a male individual, comprising buccally, sublingually, or intranasally administering to the individual, on demand, a pharmaceutical formulation containing an amount of an active agent selected from the group consisting of clomipramine and pharmacologically acceptable acid addition salts thereof effective to delay the onset of ejaculation by the individual during sexual activity.

40. The method of claim 39, wherein the active agent is administered in an amount of from about 1 mg to about 300 mg.

41. The method of claim 40, wherein the active agent is administered in an amount of from about 20 mg to about 200 mg.

42. The method of claim 41, wherein the active agent is administered in an amount of from about 25 mg to about 100 mg.

43. The method of claim 39, wherein the formulation further comprises an additional active agent.

44. A pharmaceutical dosage form for delaying the onset of ejaculation in a male individual, comprising a rapid-release formulation containing an active agent selected from the group consisting of clomipramine and pharmacologically acceptable acid addition salts thereof in an amount effective to delay the onset of ejaculation by the individual during sexual activity, wherein the dosage form releases the active agent at a rate effective to provide a systemically effective level of the agent within 3.5 hours of administration to a patient.

45. The pharmaceutical dosage form of claim 44, wherein the active agent is clomipramine.

46. The pharmaceutical dosage form of claim 45, wherein the active agent is an acid addition salt of clomipramine.

47. The pharmaceutical dosage form claim 46, wherein the active agent is clomipramine hydrochloride.

48. The pharmaceutical dosage form of claim 44, in unit dose form.

49. The pharmaceutical dosage form of claim 48, wherein the active agent is present in an amount of from about 1 mg to about 300 mg.

50. The pharmaceutical dosage form of claim 49, wherein the active agent is present in an amount of from about 20 mg to about 200 mg.

51. The pharmaceutical dosage form of claim 50, wherein the active agent is present in an amount of from about 25 mg to about 100 mg.

52. The pharmaceutical dosage form of claim 44, in the form of a rapidly disintegrating tablet.

53. The pharmaceutical dosage form of claim 44, in the form of an effervescent tablet.

54. The pharmaceutical dosage form of claim 44, in the form of an open matrix network tablet.

55. The pharmaceutical dosage form of claim 44, in the form of a sublingual tablet.

56. The pharmaceutical dosage form of claim 44, in the form of a buccal tablet.

57. The pharmaceutical dosage form of claim 44 in the form of a sublingual spray.

58. The pharmaceutical dosage form of claim 44, in the form of an inhaler.

59. The pharmaceutical dosage form of claim 44, in the form of a gum.

60. The pharmaceutical dosage form of claim 44, comprising an intranasal solution.

61. The pharmaceutical dosage form of claim 44, further comprising an additional active agent.

62. The pharmaceutical dosage form of claim 61, wherein the additional active agent is selected from the group consisting of amesergide, amineptine, amitriptyline, amoxapine, benactyzine, brofaromine, bupropion, butriptyline, cianopramine, citalopram, clorgyline, clovoxamine, demexiptiline, desipramine, dibenzepin, dimetacrine, dothiepin, doxepin, etoperidone, femoxetine, fezolamine, fluoxetine, fluvoxamine, ifoxetine, imipramine, iprindole, iso-carboxazid, levoprotiline, lofepramine, maprotiline, medifoxamine, melitracen, metapramine, methylphenidate, mianserin, milnacipran, minaprine, mirtazapine, moclobemide, nefazodone, nialamide, nomifensine, nortriptyline, opipramol, oxaflozane, oxaprotiline, oxitriptan, paroxetine, phenelzine, pirlindole, propizepine, protriptyline, quinupramine, rolipram, selegiline, sertraline, setiptiline, sibutramine, teniloxazine, tianeptine, tofenacin, toloxatone, tranylcypromine, trazodone, trimipramine, tryptophan, venlafaxine, viloxazine, viqualine, zimeldine, 2-methyl serotonin, buspirone, ipsaperone, tiaspirone, gepirone, lysergic acid diethylamide, ergot alkaloids, 8-hydroxy-(2-N,N-dipropylamino)-tetraline, 1-(4-bromo-2,5-dimethoxyphenyl)-2-aminopropane, cisapride, sumatriptan, m-chlorophenylpiperazine, zacopride, mezacopride, ondansetron, granisetron, metoclopramide, tropisetron, dolasetron, trimethobenzamide, methysergide, risperidone, ketanserin, ritanserin, clozapine, amitryptiline, R(+)-α-(2,3-dimethoxyphenyl)-1-[2-(4-fluorophenyl) ethyl]-4-piperidine-methanol, azatadine, cyproheptadine, fenclonine, dexfenfluramine, fenfluramine, chlorpromazine, methoxamine, methpentermine, metaraminol, mitodrine, clonidine, apraclonidine, guanfacine, guanabenz, methyldopa, amphetamine, methamphetamine, epinephrine, norepinephrine, ethylnorepinephrine, phenylephrine, ephedrine, pseudo-ephedrine, pemoline, naphazoline, tetrahydrozoline, oxymetazoline, xylometazoline, phenylpropanolamine, phenylethylamine, dopamine, dobutamine, colterol, isoproterenol, isotharine, metaproterenol, terbutaline, tyramine, hydroxyamphetamine, ritodrine, prenalterol, albuterol, isoetharine, pirbuterol, bitolterol, fenoterol, formoterol, procaterol, salmeterol, mephenterine, propylhexedrine, phenoxybenzamine, phentolamine, tolazoline, prazosin, terazosin, doxazosin, trimazosin, yohimbine, labetalol, urapidil, alfuzosin, bunazosin, tamsulosin, chlorpromazine, haloperidol, phenothiazines, butyrophenones, pro-pranolol, nadolol, timolol, pindolol, metoprolol, atenolol, esmolol, acebutolol, bopindolol, carteolol, oxprenolol, penbutolol, carvedilol, medroxalol, naftopidil, bucindolol, levobunolol, metipranolol, bisoprolol, nebivolol, betaxolol, carteolol, celiprolol, sotalol, propafenone, indoramin, bethanidine, debrisoquine, guabenxan, guanadrel, guanazodine, guanethidine, guanoclor, guanoxan, alprazolam, brotizolam, chlordiazepoxide, clobazepam, clonazepam, clorazepate, demoxepam, diazepam, estazolam, flurazepam, halazepam, lorazepam, midazolam, nitrazepam, nordazapam, oxazepam, prazepam, quazepam, temazepam, triazolam, pharmaceutically acceptable salts thereof, and combinations of any of the foregoing.

63. The pharmaceutical dosage form of claim 62, wherein the additional active agent is selected from the group consisting of alprazolam, brotizolam, chlordiazepoxide, clobazepam, clonazepam, clorazepate, demoxepam, diazepam, estazolam, flurazepam, halazepam, lorazepam, midazolam, nitrazepam, nordazapam, oxazepam, prazepam, quazepam, temazepam, triazolam, and pharmaceutically acceptable salts thereof.

64. The pharmaceutical dosage form of claim 62, wherein the additional active agent is selected from the group consisting of fluoxetine, fluvoxamine, paroxetine, sertraline, and pharmaceutically acceptable salts thereof.

65. A pharmaceutical dosage form for delaying the onset of ejaculation in a male individual, comprising a rapid-release formulation containing an active agent selected from the group consisting of clomipramine and pharmacologically acceptable acid addition salts thereof in an amount effective to delay the onset of ejaculation by the individual during sexual activity, wherein the dosage form is selected from the group consisting of a rapidly disintegrating tablet, an effervescent tablet, an open matrix network tablet, a sublingual tablet, a buccal tablet, a sublingual spray, an inhaler, a gum, or an intranasal solution.

66. The pharmaceutical dosage form of claim 65, wherein the dosage form is selected from the group consisting of a rapidly disintegrating tablet, an effervescent tablet, an open matrix network tablet, and a sublingual tablet.

67. The pharmaceutical dosage form of claim 65, wherein the dosage form is a buccal tablet.

68. The pharmaceutical dosage form of claim 65, wherein the active agent is present in an amount of from about 1 mg to about 300 mg.

69. The pharmaceutical dosage form of claim 68, wherein the active agent is present in an amount of from about 20 mg to about 200 mg.

70. The pharmaceutical dosage form of claim 69, wherein the active agent is present in an amount of from about 25 mg to about 100 mg.

71. A pharmaceutical dosage form for delaying the onset of ejaculation in a male individual, comprising a rapid-release formulation containing an active agent selected from the group consisting of pharmacologically acceptable acid addition salts of clomipramine, in an amount effective to delay the onset of ejaculation by the individual during sexual activity.

* * * * *